United States Patent
Rakshit et al.

(10) Patent No.: US 10,898,107 B2
(45) Date of Patent: Jan. 26, 2021

(54) SYSTEM AND METHOD FOR PULMONARY HEALTH MONITORING

(71) Applicant: Tata Consultancy Services Limited, Mumbai (IN)

(72) Inventors: Raj Rakshit, Kolkata (IN); Arijit Sinharay, Kolkata (IN); Parijat Dilip Deshpande, Kolkata (IN); Tapas Chakravarty, Kolkata (IN); Arpan Pal, Kolkata (IN); Deb Kumar Ghosh, Kolkata (IN); Shreyasi Datta, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 608 days.

(21) Appl. No.: 15/809,403

(22) Filed: Nov. 10, 2017

(65) Prior Publication Data

US 2018/0220934 A1    Aug. 9, 2018

(30) Foreign Application Priority Data

Nov. 11, 2016   (IN) .............................. 201621038666

(51) Int. Cl.
*A61B 5/097* (2006.01)
*A61B 5/087* (2006.01)
(Continued)

(52) U.S. Cl.
CPC ............ *A61B 5/097* (2013.01); *A61B 5/0004* (2013.01); *A61B 5/0803* (2013.01); *A61B 5/087* (2013.01);
(Continued)

(58) Field of Classification Search
CPC ..... A61B 5/097; A61B 5/7242; A61B 5/0803; A61B 5/7267; A61B 5/091; A61B 5/087;
(Continued)

(56) References Cited

U.S. PATENT DOCUMENTS 4,736,750 A * 4/1988 Valdespino .......... A61B 5/0871
600/538
6,099,481 A * 8/2000 Daniels .................. A61B 5/083
128/204.23
(Continued)

FOREIGN PATENT DOCUMENTS

EP           0100584 B1 * 7/1986 ............. G01F 1/667
WO    WO 2007/124126 A2    11/2007

OTHER PUBLICATIONS

Ioannis I. Spyroglou, et. al., "Evaluation of a prediction model based on ridge regression for asthma persistence in preschool children", International Journal of Mathematical Models and Methods in Applied Sciences, vol. 9, p. 581-590 (Year: 2015).*

*Primary Examiner* — Eric F Winakur
*Assistant Examiner* — Abid A Mustansir
(74) *Attorney, Agent, or Firm* — Finnegan, Henderson, Farabow, Garrett & Dunner, LLP

(57) ABSTRACT

A pulmonary health monitoring system aims at assessing pulmonary health of subjects. Conventional techniques used for pulmonary health monitoring are not convenient to the subjects and needs considerable cooperation from the subjects. But, there is a challenge in utilizing the conventional devices to the subjects not capable of providing considerable cooperation. The present disclosure includes a blow device applicable to all kind of subjects and doesn't need cooperation from the subjects. Further, in the present disclosure, the blow device generates a phase shifted signal corresponding to a breathe signal and the phase shifted signal is further processed to extract a set of physiological features. Further, pulmonary health of a subject is analyzed by processing the set of physiological features based on a ridge regression based machine learning technique.

7 Claims, 10 Drawing Sheets

(51) Int. Cl.
*A61B 5/091* (2006.01)
*A61B 5/00* (2006.01)
*A61B 5/08* (2006.01)

(52) U.S. Cl.
CPC ............ *A61B 5/091* (2013.01); *A61B 5/7203* (2013.01); *A61B 5/725* (2013.01); *A61B 5/7242* (2013.01); *A61B 5/7267* (2013.01); *A61B 5/7278* (2013.01); *A61B 5/7275* (2013.01); *A61B 2562/0204* (2013.01)

(58) Field of Classification Search
CPC ..... A61B 5/725; A61B 5/7203; A61B 5/7278; A61B 5/0004; A61B 2562/0204; A61B 5/7275
See application file for complete search history.

(56) References Cited

U.S. PATENT DOCUMENTS

| | | |
|---|---|---|
| 8,870,785 B2 | 10/2014 | Muehlsteff et al. |
| 2015/0164375 A1 | 6/2015 | Schindhelm et al. |

* cited by examiner

— ULTRASOUND SIGNAL FLOW DIRECTION
-· BREATH SIGNAL FLOW DIRECTION

SYSTEM AND METHOD FOR PULMONARY HEALTH MONITORING

PRIORITY CLAIM

The present application claims priority to Indian provisional specification (Title: SYSTEM AND METHOD FOR PULMONARY HEALTH MONITORING) Application No. (201621038666), filed in India on Nov. 11, 2016. The entire contents of the aforementioned application are incorporated herein by reference.

TECHNICAL FIELD

The embodiments herein generally relates, in general, to health monitoring and, in particular, to a system and method for pulmonary health monitoring.

BACKGROUND

A pulmonary disease is an abnormal condition in respiratory system. Examples of the pulmonary disease includes an Obstructive Airway Disease (OAD) which is affecting urban and rural demographics worldwide. The OAD includes Chronic Obstructive Pulmonary Disease (COPD), pneumothorax, Obstructive Sleep Apnea (OSA), asthma, bronchiectasis and bronchitis. Generally, the OADs are not completely curable in later stages and necessitates diagnosis in earlier stages. Also, there is a challenge in differentiating between the OADs. For example, COPD can be misdiagnosed as asthma.

Conventionally, pulmonary diseases are diagnosed based on a spirometry test. The spirometry test requires cooperation of a user, for example, the user may be asked to take deepest breath and forcefully exhale through a flow monitoring device. Due to dependency of cooperation of the user, there is a challenge in using the spirometry test for a plurality of users. The plurality of subjects includes a subject suffering from hemoptysis of unknown origin, a subject suffering from pneumothorax, a subject having unstable cardio-vascular status, a subject suffering from thoracic aneurysms, a subject suffering from abdominal aneurysms, a subject suffering from cerebral aneurysms, a subject after an eye surgery, a subject after thoracic surgery, a subject after abdominal surgery and children under six years. Moreover, the conventional spirometry test methods may be associated with high costs, sensitivity and noise rejection.

SUMMARY

Embodiments of the present disclosure present technological improvements as solutions to one or more of the above-mentioned technical problems recognized by the inventors in conventional systems. For example, in one embodiment, a method for pulmonary health monitoring is provided. The method includes receiving, an interference signal, wherein the interference signal is a reference excitation signal, modified in accordance with a first signal, by the one or more hardware processors. Further, the method includes generating, a phase shifted signal by comparing the reference excitation signal and the interference signal, by the one or more hardware processors. Furthermore, the method includes generating, a signal voltage corresponding to the phase shifted signal by processing the phase shifted signal, by the one or more hardware processors. Furthermore, the method includes generating, a flow signal associated with the signal voltage by utilizing a set of peaks and a set of troughs associated with the signal voltage, wherein the set of peaks and the set of troughs are obtained by processing the signal voltage, by the one or more hardware processors. Furthermore, the method includes generating, a volumetric signal by processing the flow signal based on a trapezoidal rule based numerical integration technique, by the one or more hardware processors. Furthermore, the method includes extracting, a set of physiological features associated with the volumetric signal, by the one or more hardware processors. Furthermore, the method includes assessing, pulmonary health by analyzing the set of physiological features based on a ridge regression based machine learning technique, by the one or more hardware processors.

In another aspect, a system for pulmonary health monitoring is provided. The system includes one or more memories comprising programmed instructions and a repository for storing a first signal, a reference excitation signal, an interference signal, a phase shifted signal and a set of features associated with a volumetric signal, one or more hardware processors operatively coupled to the one or more memories, wherein the one or more hardware processors are capable of executing the programmed instructions stored in the one or more memories, a blow device to generate a phase shifted signal corresponding to the first signal, wherein the blow device comprises a flow device and a breathe signal unit and a signal analysis unit, wherein the signal analysis unit is configured to: generate, a signal voltage corresponding to the phase shifted signal by processing the phase shifted signal. Further, signal analysis unit is configured to generate, a flow signal associated with the signal voltage by utilizing a set of peaks and a set of troughs associated with the signal voltage, wherein the set of peaks and the set of troughs are obtained by processing the signal voltage. Furthermore the signal analysis unit is configured to generate, a volumetric signal by processing the flow signal based on a trapezoidal rule based numerical integration technique. Furthermore, the signal analysis unit is configured extract, a set of physiological features associated with the volumetric signal. Finally, the signal analysis unit is configured to assess, pulmonary health by analyzing the set of physiological features based on a ridge regression based machine learning technique.

In yet another aspect, a computer program product comprising a non-transitory computer-readable medium having embodied therein a computer program for system and method for pulmonary health monitoring, is provided. The computer readable program, when executed on a computing device, causes the computing device to receive, an interference signal, wherein the interference signal is a reference excitation signal, modified in accordance with a first signal. Further, the computer readable program, when executed on a computing device, causes the computing device to generate, a phase shifted signal by comparing the reference excitation signal and the interference signal. Furthermore, the computer readable program, when executed on a computing device, causes the computing device to generate, a signal voltage corresponding to the phase shifted signal by processing the phase shifted signal. Furthermore, the computer readable program, when executed on a computing device, causes the computing device to generate, a flow signal associated with the signal voltage by utilizing a set of peaks and a set of troughs associated with the signal voltage, wherein the set of peaks and the set of troughs are obtained by processing the signal voltage. Furthermore, the computer readable program, when executed on a computing device, causes the computing device to generate, a volumetric signal by processing the flow signal based on a trapezoidal rule based numerical integration technique. Furthermore, the computer readable program, when executed on a computing device, causes the computing device to extract, a set of physiological features associated with the volumetric signal. Furthermore, the computer readable program, when executed on a computing device, causes the computing device to assess, pulmonary health by analyzing the set of physiological features based on a ridge regression based machine learning technique.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

Figure 1:
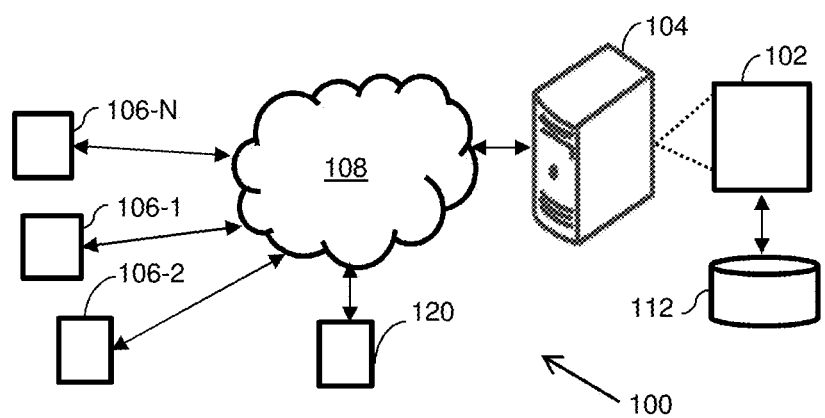
FIG. 1 illustrates a network environment implementing a system and method for a pulmonary health monitoring, according to some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The present subject matter overcomes the limitations of the conventional pulmonary health monitoring techniques by utilizing a blow device to generate a phase shifted signal corresponding to a first signal. In an embodiment, the first signal can be a breathe signal. For brevity of description, the first signal can be alternatively referred as breathe signal. Further, a signal voltage corresponding to the phase shifted signal is generated and the signal voltage is converted to a flow signal by processing the signal voltage. Further, the flow signal is converted into a volumetric signal and a set of physiological features are extracted from the flow signal and the volumetric signal. Further, pulmonary health of a subject is analyzed by processing the set of physiological features based on a regression based machine learning technique. An implementation of the system and method for pulmonary health monitoring is described further in detail with reference to FIGS. 1 through 12.

Referring now to the drawings, and more particularly to FIGS. 1 through 12, where similar reference characters denote corresponding features consistently throughout the figures, there are shown preferred embodiments and these embodiments are described in the context of the following exemplary system and/or method.

FIG. 1 illustrates a network environment 100 implementing a system 102 for pulmonary health monitoring, according to an example embodiment of the present disclosure. The system for pulmonary health monitoring 102, hereinafter referred to as the system 102, is configured to receive an interference signal corresponding to the breathe signal and to generate the phase shifted signal by processing the interference signal by using a blow device 120. The system 102 may be embodied in a computing device, for instance a computing device 104.

Although the present disclosure is explained considering that the system 102 is implemented on a server, it may be understood that the system 102 may also be implemented in a variety of computing systems, such as a laptop computer, a desktop computer, a notebook, a workstation, a cloud-based computing environment and the like. In one implementation, the system 102 may be implemented in a cloud-based environment. It will be understood that the system 102 may be accessed by multiple users through one or more user devices 106-1, 106-2 . . . 106-N, collectively referred to as user devices 106 hereinafter, or applications residing on the user devices 106. Examples of the user devices 106 may include, but are not limited to, a portable computer, a personal digital assistant, a handheld device, a Smartphone, a Tablet Computer, a workstation and the like. The user devices 106 are communicatively coupled to the system 102 through a network 108.

In an embodiment, the network 108 may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 108 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 108 may include a variety of network devices, including routers, bridges, servers, computing devices, storage devices. The network devices within the network 108 may interact with the system 102 through communication links.

As discussed above, the system 102 may be implemented in a computing device 104, such as a hand-held device, a laptop or other portable computer, a tablet computer, a mobile phone, a PDA, a smartphone, and a desktop computer. The system 102 may also be implemented in a workstation, a mainframe computer, a server, and a network server. In an embodiment, the system 102 may be coupled to a data repository, for example, a repository 112. The repository 112 may store data processed, received, and generated by the system 102. In an alternate embodiment, the system 102 may include the data repository 112. The components and functionalities of the system 102 are described further in detail with reference to FIG. 2.

Figure 2:
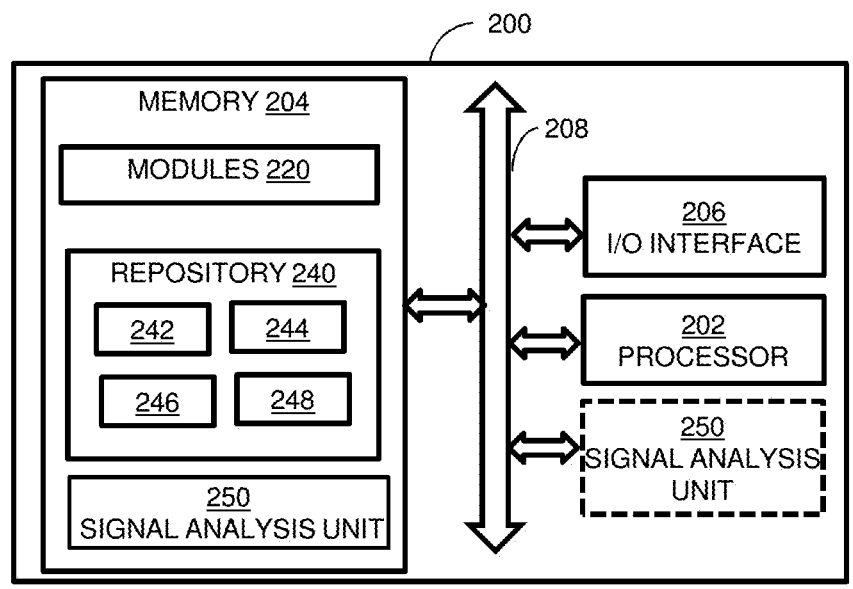
FIG. 2 illustrates a block diagram of the system for the pulmonary health monitoring, according to some embodiments of the present disclosure.

FIG. 2 illustrates a block diagram of the system for pulmonary health monitoring, according to some embodiments of the present disclosure. The pulmonary health monitoring system 200 (hereinafter referred to as system 200) may be an example of the system 102 (FIG. 1). In an example embodiment, the system 200 may be embodied in, or is in direct communication with the system, for example the system 102 (FIG. 1). The system 200 includes or is otherwise in communication with one or more hardware processors such as a processor 202, at least one memory such as a memory 204, an I/O interface 206 and a signal analysis unit 250. In an embodiment, the signal analysis unit 250 can be implemented as a standalone unit in the system 200 comprising a signal processing unit (not shown in FIG. 2), a physiological feature extraction unit (not shown in FIG. 2), and a Locally Weighted Learning (LWL) based classification unit (not shown in FIG. 2). In another embodiment, the signal analysis unit 250 can be implemented as a module in the memory 204 comprising the signal processing unit (not shown in FIG. 2), the physiological feature extraction unit (not shown in FIG. 2), and the LWL based classification unit (not shown in FIG. 2). The processor 202, memory 204, and the I/O interface 206 may be coupled by a system bus such as a system bus 208 or a similar mechanism.

The I/O interface 206 may include a variety of software and hardware interfaces, for example, a web interface, a graphical user interface, and the like. The interfaces 206 may include a variety of software and hardware interfaces, for example, interfaces for peripheral device(s), such as a keyboard, a mouse, an external memory, a camera device, and a printer. Further, the interfaces 206 may enable the system 102 to communicate with other devices, such as web servers and external databases. The interfaces 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 206 may include one or more ports for connecting a number of computing systems with one another or to another server computer. The I/O interface 206 may include one or more ports for connecting a number of devices to one another or to another server.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220 and the signal analysis unit 250. The modules 220 may include routines, programs, objects, components, data structures, and so on, which perform particular tasks or implement particular abstract data types.

The memory 204 also includes module(s) 220 and a data repository 240. The module(s) 220 include programs or coded instructions that supplement applications or functions performed by the pulmonary health monitoring system 200. The modules 220, amongst other things, can include routines, programs, objects, components, and data structures, which perform particular tasks or implement particular abstract data types. The modules 220 may also be used as, signal processor(s), state machine(s), logic circuitries, and/or any other device or component that manipulates signals based on operational instructions. Further, the modules 220 can be used by hardware, by computer-readable instructions executed by a processing unit, or by a combination thereof. The modules 220 can include various sub-modules (not shown). The modules 220 may include computer-readable instructions that supplement applications or functions performed by the pulmonary health monitoring system 200.

The data repository 240 may include an interference signal database 242, a phase shifted signal database 244, a respiration signal database 246 and other data 248. Further, the other data 248 amongst other things, may serve as a repository for storing data that is processed, received, or generated as a result of the execution of one or more modules in the module(s) 220 and the modules associated with the signal analysis unit 250. The repository 240 is further configured to maintain a set of features associated with the signals stored in the data repository 240.

Although the data repository 240 is shown internal to the pulmonary health monitoring system 200, it will be noted that, in alternate embodiments, the data repository 240 can also be implemented external to the pulmonary health monitoring system 200, where the data repository 240 may be stored within a database (not shown in FIG. 2) communicatively coupled to the pulmonary health monitoring system 200. The data contained within such external database may be periodically updated. For example, new data may be added into the database (not shown in FIG. 2) and/or existing data may be modified and/or non-useful data may be deleted from the database (not shown in FIG. 2). In one example, the data may be stored in an external system, such as a Lightweight Directory Access Protocol (LDAP) directory and a Relational Database Management System (RDBMS). In another embodiment, the data stored in the data repository 240 may be distributed between the pulmonary health monitoring system 200 and the external database.

Figure 3:
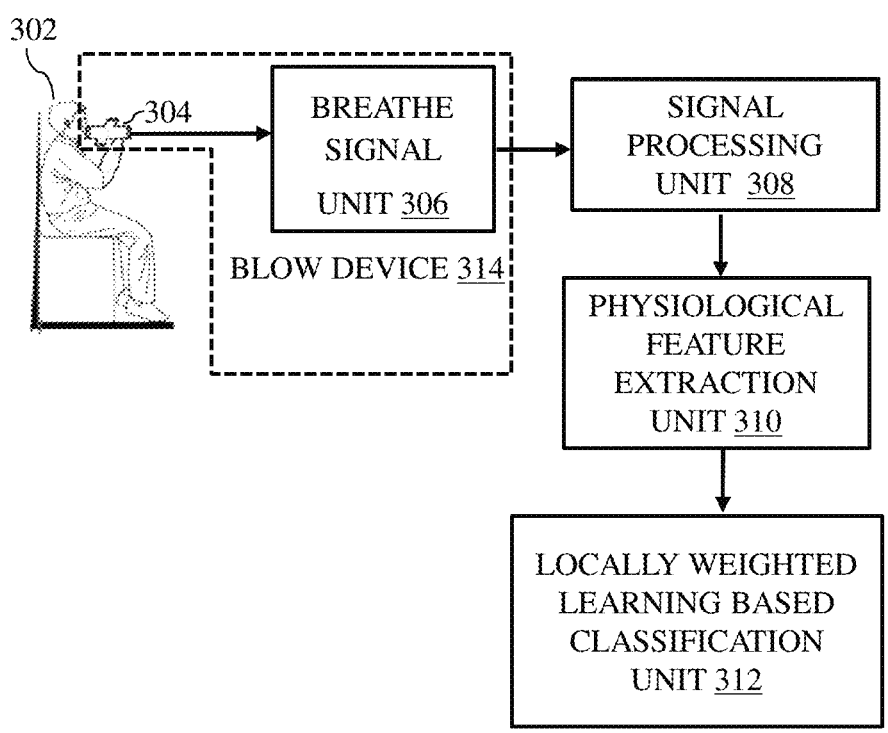
FIG. 3 illustrates an example architecture for the pulmonary health monitoring system, according to some embodiments of the present disclosure.

FIG. 3 illustrates an example architecture for the pulmonary health monitoring system, according to some embodiments of the present disclosure. Here, the breathe signal from the subject 302 is allowed to flow through a blow device 314. In an embodiment, the breathe signal can be a tidal breathe signal and the blow device 314 is configured to generate the phase shifted signal corresponding to the tidal breathe signal. The blow device 314 is further explained with reference to FIG. 4. Further, the phase shifted signal is processed by the signal processing unit 308 to generate the volumetric signal. Here, the signal voltage corresponding to the phase shifted signal is generated and the signal voltage is further processed to generate the flow signal corresponding to the signal voltage. Further, the flow signal is converted into the volumetric signal. Further, the set of physiological features associated with the volumetric signal and the flow signal are extracted by the physiological feature extraction unit 310. Further, the set of physiological features are analyzed by the LWL based classification unit 312 to assess pulmonary health of the subject.

The signal analysis unit 250 of the pulmonary health monitoring system 200 can be configured to receive the interference signal, wherein the interference signal is a reference excitation signal, modified in accordance with the breathe signal. A plurality of techniques can be utilized for sensing an air flow. For example, a mechanical, a pressure, an optical, a thermal, a vortex, an electromagnetic, a Doppler and an ultrasound based flow meters can be utilized for sensing the air flow. Further, the ultrasound based sensing is most accurate and capable of providing a directional flow information associated with the air flow. Here, the interference signal is received by utilizing the flow pipe 304 (refer FIG. 3) associated with the blow device 314. The blow device 314 is further explained with reference to FIG. 4.

Figure 4:
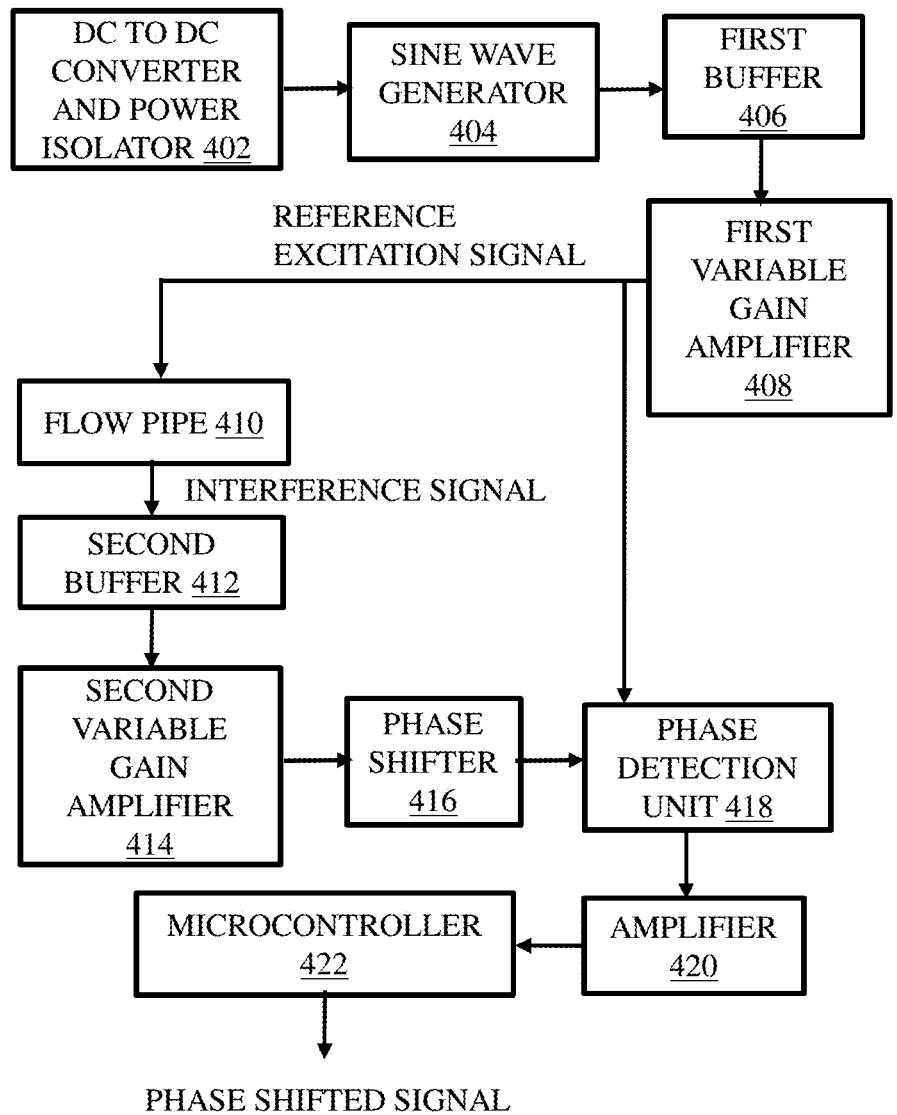
FIG. 4 illustrates an example architecture of a blow device, according to some embodiments of the present disclosure.

In an embodiment, FIG. 4 illustrates an example architecture of the blow device 314, according to some embodiments of the present disclosure. Now referring to FIG. 4, the blow device 314 includes the flow pipe 304 and a breathe signal unit 306. In an embodiment, the breathe signal unit includes a DC (Direct Current) to DC converter and a plurality of components. Here the DC to DC converter and power isolator 402 is configured to provide power supply to the plurality of components. The plurality of components includes a sine wave generator 404, a first buffer 406, a first variable gain amplifier 408, a second buffer 412, a second variable gain amplifier 414, a phase shifter 416, a phase detection unit 418, an amplifier 420 and a microcontroller 422. Additionally, the DC to DC converter and power isolator 402 is configured to provide power supply to a transmitter transducer $T_x$ and a receiver transducer $R_x$ hosted to the flow pipe 304.

In an embodiment, the transmitter transducer $T_x$ can be a 40 kHz air coupled ultrasonic transmitter transducer and the receiver transducer $R_x$ can be a 40 kHz air coupled ultrasonic receiver transducer. The 40 kHz air coupled ultrasonic transmitter transducer is driven by the sine wave generator 404, for example a 40 kHz sine wave generator. Here, the sine wave generator is connected to the first buffer 406 to obtain a buffered sine wave and the first variable gain amplifier to amplify the buffered sine wave. The buffered sine wave is a reference excitation signal. The reference excitation signal is further passed through the flow pipe 410 and the interference signal is generated. Here, the reference excitation signal is interfered by the breathe signal passed through a mouth piece 506 (refer FIG. 5A) and a blow pipe 508 (refer FIG. 5A) associated with the flow pipe 410.

Further, the signal analysis unit 250 of the pulmonary health monitoring system 200 can be further configured to generate the phase shifted signal by processing the interference signal. Now referring to FIG. 4, the interference signal from the flow pipe 410 is received by the second buffer 412 and further amplified by the second variable gain amplifier 414 to obtain an amplified interference signal. Further, the amplified interference signal is adjusted according to an idle operating point to compensate a default phase shift and to generate a phase shifted voltage by the phase shifter unit 416. Further, the phase detection unit 418 compares the phase shifted voltage and the reference excitation signal to obtain a Direct Current (DC) voltage corresponding to a phase shift. Further, the DC voltage corresponding to the phase shift is amplified by the amplifier 420 and further converted to a digital phase shifted signal by the microcontroller 422. For brevity of description, the digital phase shifted signal can be alternatively referred as the phase shifted signal.

Figure 5A:
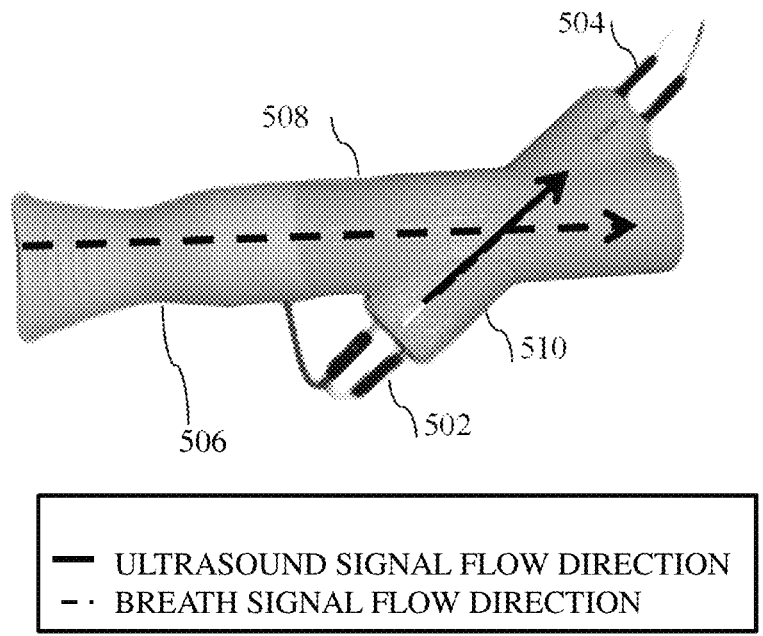
FIG. 5A illustrates an example physical construction of a flow pipe, according to some embodiments of the present disclosure.
Figure 5B:
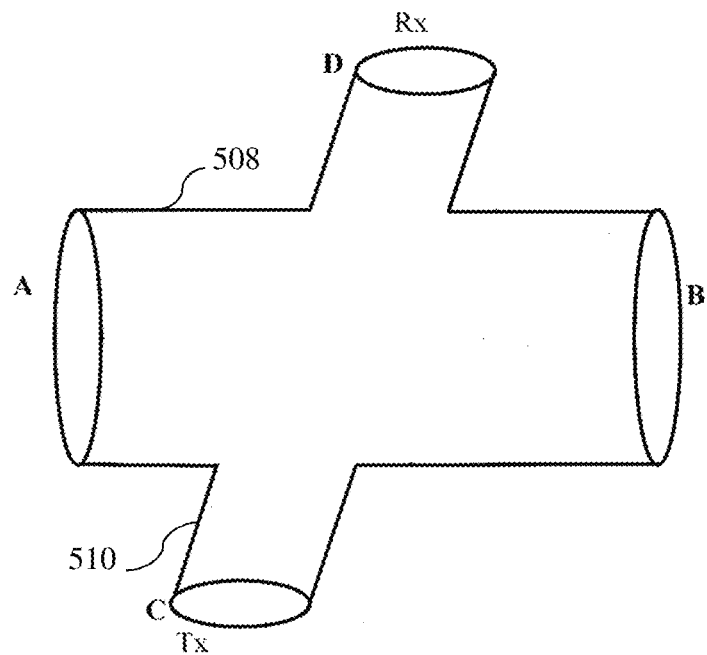
FIG. 5B illustrates an example diagrammatic sketch of the flow pipe, according to some embodiments of the present disclosure.

In an embodiment, the flow pipe 410 as mentioned in FIG. 4 is further explained with reference to FIG. 5A and FIG. 5B. Here, FIG. 5A illustrates an example physical construction of the flow pipe 304, according to some embodiments of the present disclosure. FIG. 5B illustrates the example diagrammatic sketch of the flow pipe 304, according to some embodiments of the present disclosure. Now referring to FIG. 5A, the flow pipe 304 includes a first hollow pipe 508 cross coupled to a second hollow pipe 510. The first hollow pipe 508 is inclined to the second hollow pipe 510 to a predefined angle. A disposable mouth piece 506 is detachably attached to a first end of the first hollow pipe 508. A transmitter transducer $T_x$ 502, for example an ultrasonic transmitter transducer is hosted at a first end of the second hollow pipe 510. A receiver transducer $R_x$ 504, for example an ultrasonic receiver transducer is hosted at a second end of the second hollow pipe 510. In an embodiment, the first hollow pipe 508 and the second hollow pipe 510 can be cylindrical in shape. In an embodiment, the first hollow pipe 508 and the second hollow pipe 510 can vary in diameter. For brevity of description, the first hollow pipe 508 can be alternatively referred to as a blow pipe and the second hollow pipe 510 can be alternatively referred to as a sensor pipe. Here, the breathe signal from the subject is passed to the blow pipe 508 through the mouth piece 506. A flow direction of the breathe signal in the blow pipe 508 is represented as a dotted line and a flow direction of an ultrasound from the transmitter transducer 502 to the receiver transducer 504 is represented as a solid line. In an embodiment, the blow-pipe 304 is 3Dimensional printed pipe.

Now referring to FIG. 5B, the first end of the first hollow pipe 508 is represented as 'A' and a second end of the first hollow pipe 508 is represented as 'B'. A signal path associated with the blow pipe 508 is represented as A-B. Further, the first end of the second hollow pipe 510 is represented as 'C' and the second end of the second hollow pipe 510 is represented as 'D'. A signal path associated with the sensor pipe 510 is represented as C-D. In an embodiment, a radius $r_1$ associated with the first hollow pipe 508 can be 11.88 millimeter and a radius $r_2$ associated with the second hollow pipe 510 can be 8.89 millimeter. In an embodiment, a length $l_1$ associated with the first hollow pipe 508 can be at 100 millimeter and a length $l_2$ associated with the second hollow pipe 510 can be 68 millimeter. In an embodiment, the first hollow pipe 508 is inclined to the second hollow pipe 510 to the angle θ=40 degree. The angle θ=40 degree can provide maximum dynamic range coverage.

In an embodiment, for a given distance 'D1' between the transmitter transducer $T_x$ and the receiver transducer $R_x$, hosted in the sensor pipe 510, a change in sound speed due to inspiration and expiration (for example, the breathe signal) results in a proportionate phase difference ∅ between a transmitted signal and a received signal. Here, the transmitted signal is the reference excitation signal and the received signal is the interference signal. The phase difference ∅ is given by the equation 1, $$\phi = \frac{2\pi t}{T} = \frac{2\pi t}{T}\left(\frac{D1}{v_{sound} + v_p}\right) \quad (1)$$

Where, T is a periodicity of the reference excitation signal, $v_{sound}$ is a velocity of the reference excitation signal, $v_p$ is a velocity component of the medium (say, due to respiration) parallel to sound travel path. Here, a change in phase-difference ∂∅ can be related to change in the respiration velocity ∂v as given in equation 2, $$\partial \phi = \frac{2\pi D1}{T} \frac{\partial v_p}{(v_{sound} + v_p)^2} = K \partial v_p \quad (2)$$

Since speed of sound is much greater than tidal breathing component, (for example, a speed of a tidal breathe signal≈0.1 to 10 m/s), $(v_{sound}+v_p)^2 \approx v_{sound}^2$ thus resulting in $$K = -\frac{2\pi D1}{Tv_{sound}^2}.$$

Equation 2 illustrates a relationship between a component of inspiration/expiration velocity and the signal in the sensor pipe path. Here, $\partial v_p$ is directly proportional to phase shift ∂∅ of the signal in the sensor pipe. Additionally, the sensitivity of the breathe signal is directly proportional to ultrasound frequency. Hence, for a given flow velocity, larger phase shift is obtained for increasing frequency (f=1/T).). In an embodiment, the system 200 has been operated with 40 kHz since 40 kHz air coupled transducers are widely available and cost effective.

Further, the signal analysis unit 250 of the pulmonary health monitoring system 200 can be configured to generate the signal voltage corresponding to the phase shifted signal by processing the phase shifted signal. In an embodiment, a breathe signal velocity (for example, a respiration signal velocity) associated with the signal path C-D is given by the equation 3, $$v_p = v \cos \theta \quad (3)$$

Where, v is the respiration signal (breathe signal) velocity applied by the subject at the end A (refer FIG. 5B) and e is the angle between the blow pipe 508 and the sensor pipe 510. Here, the change in the phase-difference ∂∅ between the reference excitation signal generated from the end 'C' of the sensor pipe 510 and the interference signal received at the end 'D' of the sensor pipe 510 is related to the change in velocity of the respiration signal as in equation 2 and can be rewritten corresponding to the blow-pipe as given in equation 4, $$\phi = -\frac{2\pi l_2}{Tv_{sound}^2} \partial v_p \quad (4)$$

Where, $l_2$ is the distance between the transmitter transducer $T_x$ and the receiver transducer $R_x$ hosted in the sensor pipe 510. Further, the reference excitation signal and the interference signal are compared by the phase detection unit 418 (refer FIG. 4) and the DC voltage corresponding to the phase shift is obtained. The DC voltage corresponding to the phase shift is represented in equation 5, $$V_{Phase} = K_\phi[\emptyset_{INA} - \emptyset_{INB}] \quad (5)$$

Where, $K_\emptyset$ is the phase gradient given as mV/rad. $\emptyset_{INA}$ is a phase value associated with the reference excitation signal and $\emptyset_{INB}$ is a phase value associated with the interference signal. Further, $V_{Phase}$ is amplified with a variable amplification factor 'G' and the phase shifted signal is represented by equation 6, $$\partial V_{OUT} = GK_\phi[\phi_{INA} - \phi_{INB}] = GK_\phi \partial \phi = -\frac{GK_\phi 2\pi l_2}{Tv_{sound}^2}\partial v_p \quad (6)$$

$$\text{Where, } \partial V_{OUT} = -\frac{GK_\phi 2\pi l_2 \cos\theta}{Tv_{sound}^2}\partial v$$

Where, the negative sign indicates that the direction of air flow and the output voltage have opposite polarity. Thus the respiration velocity ∂v can be represented as given in equation 7, $$\partial V = \frac{Tv_{sound}^2}{GK_\phi 2\pi l_2 \cos\theta}\partial V_{OUT} = F(G, K_\phi)\partial V_{OUT} \quad (7)$$

Here, the term F (G, $K_\emptyset$) indicates the dependence of the output voltage change (for a given air flow) on the overall gain of the system as well as the phase gradient $K_\emptyset$ and other parameters are kept as constant. Further, the theoretical value for F (G, $K_\emptyset$) can be computed and the computation needs to be estimated (through calibration process) in the present set up in order to obtain respiration velocity in terms of m/sec. Further, the instantaneous flow rate, Q (m3/sec) for laminar flow is given in equation 8, $$Q = \oint v \cdot dA = v\pi \eta^2 \quad (8)$$

Where, v is the respiration signal (breathe signal) velocity obtained from equation 7 and A is a cross sectional area of the blow pipe 508. Further, equation 9 is obtained by solving equation 7 and equation 8. The equation 9 is given by, $$Q = F(G, K_\phi) V_{OUT} \pi r_1^2 \cdot 10^3 \text{ (in L/sec)} \quad (9)$$

Figure 6A:
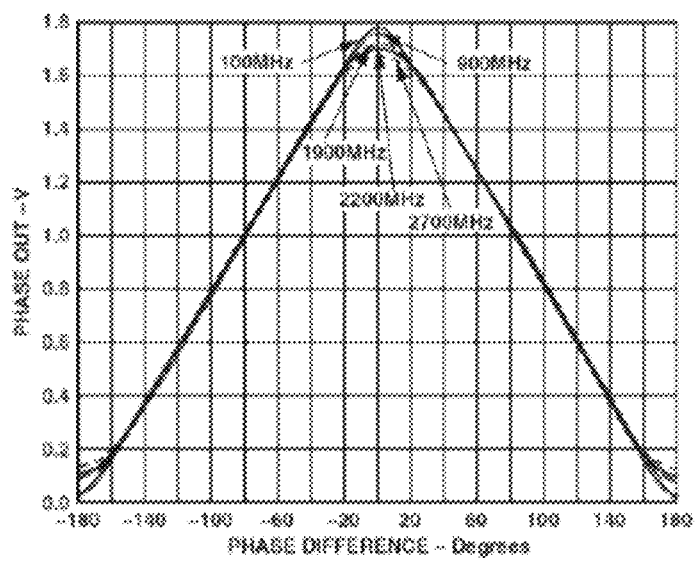
FIG. 6A illustrates an example phase characteristics curve, according to some embodiments of the present disclosure.

In an embodiment, a parameter G and a parameter $K_\phi$ are computed to derive the value of Q in an operating frequency of 40 kHz. FIG. 6A illustrates an example phase characteristic curve, according to some embodiments of the present disclosure. Now referring to FIG. 6A, the phase shift is measured in the range from 0 degree to 180 degree and the response is clear in the measured range. Here, the phase characteristics curve is plotted between the phase difference and the output phase voltage.

Figure 6B:
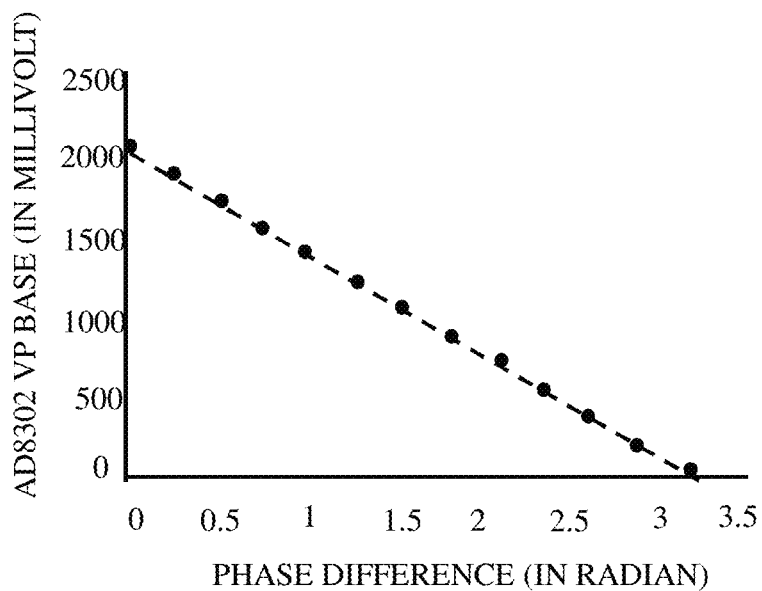
FIG. 6B illustrates an example phase response curve plotted between phase difference $\partial\theta$ measured in radians and the phase change voltage $V_{Phase}$ measured in millivolt, according to some embodiments of the present disclosure.

In an embodiment, FIG. 6B illustrates an example phase response curve plotted between phase difference ∂ϕ measured in radians and the phase change voltage $V_{Phase}$ measured in millivolt, according to some embodiments of the present disclosure. Here, the phase response curve is plotted between the 40 kHz reference excitation signal and the interference signal. The interference signal is the phase shifted reference excitation signal. The phase response is fairly linear in a range of 0 degree to 180 degree. However, the phase response is slowly gets saturated from 160 degree onwards and the measurements are taken in the range of 0 degree to 160 degree only. A slope of the curve, i.e. Kϕ, is found to be −609.55 mV/rad. Here, the operating point for idle condition (i.e. no flow condition) is considered as 90 degree (i.e. middle of the curve) so as to capture excursions (i.e. inhale and exhale) on both downward swing and upward swing without any wrapping or saturation. Additionally, 60 degree downside swing is reserved for exhale and 60 degree upward swing is reserved for inhale. In an embodiment, the reduction of 20 degree works out fine as even with forced breathing and the phase-shift remained well under 60 degree.

In an embodiment, the term F (G,$K_\phi$) relies on the system gain G and the slope $K_\phi$. Now, $K_\phi$ is computed to be 609.55 mV/rad and treated as fixed. The gain (G) of the variable gain amplifier is nominally set to 3, in an effort to achieve maximum compliance during data acquisition. Since F (G, $K_\phi$) now depends only on the variable gain G, F (G, $K_\phi$)=F (G). In an embodiment, the maximum velocity of human tidal breathing rarely exceeds 3 m/s and to gain maximum compliance of the blow device (i.e. to accommodate voluntary forceful breathing also), a maximum flow velocity is considered to be 10 m/s. Further, the maximum flow velocity is utilized for computing an optimal angle θ. Further, a magnitude of maximum change in phase is obtained by solving equation 3 and equation 4 and the magnitude of maximum change in phase is given in equation 10, $$|\partial \phi|_{max} = \frac{2\pi l_2 v_{max}}{T v_{sound}^2} \cos\theta \quad (10)$$

Figure 6C:
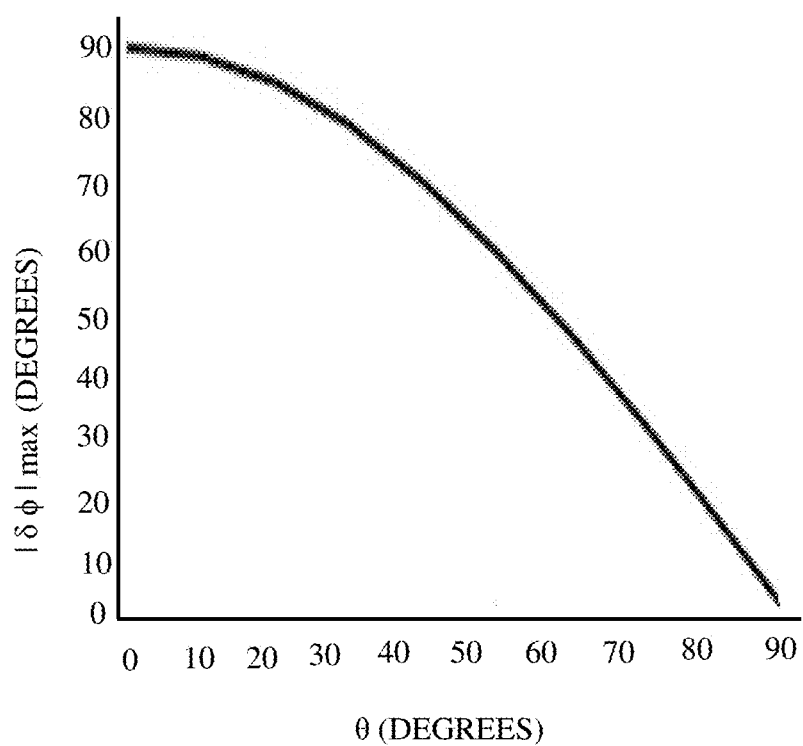
FIG. 6C illustrates an example curve showing the variation of the magnitude of maximum change in phase over varying values of the optimum angle $\theta$, for $v_{max}=10$ m/sec, according to some embodiments of the present disclosure.

In an embodiment, FIG. 6C illustrates an example curve showing the variation of the magnitude of maximum change in phase over varying values of the optimum angle θ, for $v_{max}$=10 m/sec, according to some embodiments of the present disclosure. Now referring to FIG. 6C, for the blow velocity of 10 m/sec, the blow device loses sensitivity when the optimum angle θ is nearing 90 degree. Hence, the subject is supposed to blow with higher efforts. When the optimum angle θ=90 degree, phase change is not detected. For lower values of the optimum angle θ, the phase change approaches 90 degree, which is more than maximum allowable phase swing (for example, the maximum allowable phase swing is 60 degree). If the optimum angle θ is set to 0 degree, the design of the blow pipe is not possible from design perspective since the blow pipe 508 and the sensor pipe 510 lie on the same line (refer FIG. 5A and FIG. 5B). Further, lower values of the optimum angle θ can increase the length of the sensor pipe 510 unnecessarily. When the optimum angle θ is 40 degree, the design is compact and the phase change falls around 60 degree for the upward swing and the downward swing. In an embodiment, the optimum angle θ is taken as 40 degree.

Figure 7:
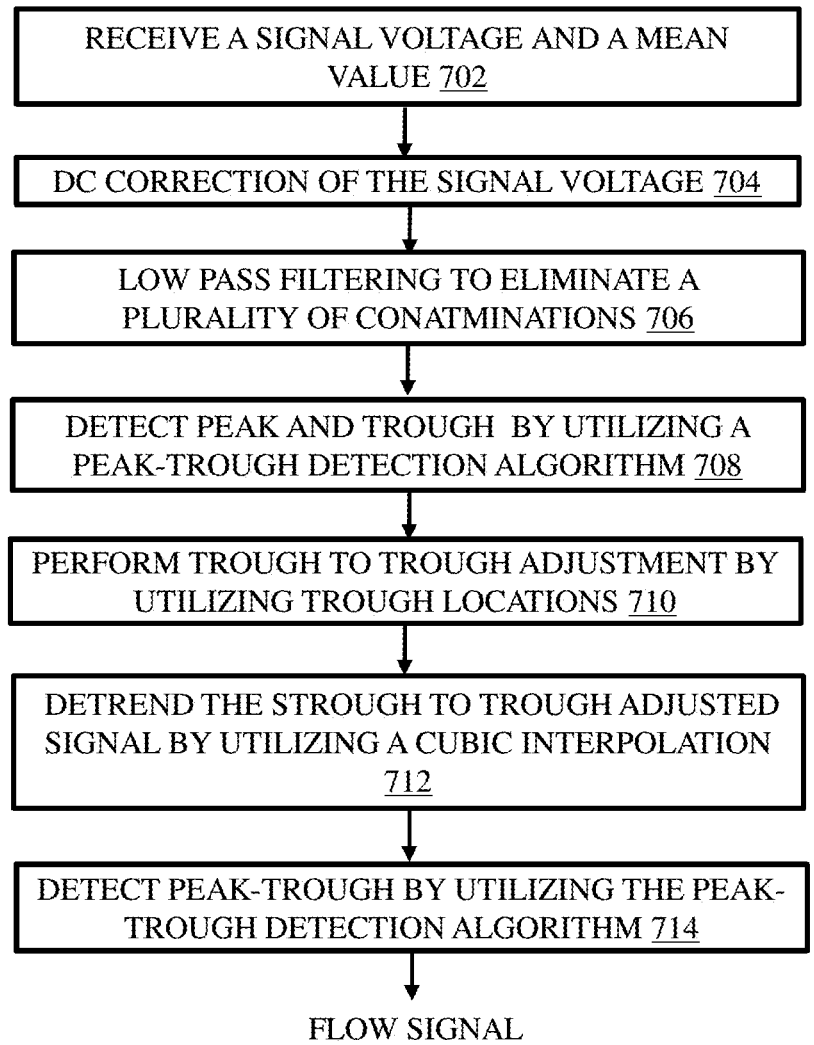
FIG. 7 illustrates an example flow diagram for processing a signal voltage to obtain a flow signal, according to some embodiments of the present disclosure.

Further the signal analysis unit 250 of the pulmonary health monitoring system 200 can be configured to generate, a flow signal associated with the signal voltage by processing the signal voltage. Initially, a respiration flow rate (in L/s) is obtained from the signal voltage $V_{OUT}$ according to equation 9. Further, FIG. 7 illustrates the example method flow for processing the signal voltage to obtain the flow signal, according to some embodiments of the present disclosure. Now referring to FIG. 7, at step 702, a mean value associated with the breathe signal and the signal voltage is received. Further, at step 704, the signal voltage is DC corrected by subtracting the mean value of the breathe signal from the signal voltage $V_{OUT}$. Further, at step 706, a low pass filtering is performed to eliminate a plurality of contaminations associated with the DC corrected signal voltage. The plurality of contaminations includes powerline interferences, body movement and other high frequency noises. In an embodiment, the low pass filtering can be a $2^{nd}$ order Infinite Impulse Response (IIR) low pass filtering with a cut off frequency 15 Hz. Further, at step 708, a set of peaks and a set of troughs associated with the low pass filtered signal voltage are identified by a peak-trough detection algorithm. The set of peaks and the set of troughs are crucial elements of inspiration-expiration (respiration or breathe) cycles. Generally, the peak-trough detection algorithm identifies a set of local maxima and a set of local minima in the low pass filtered signal. Further, at step 710, low pass filtered signal is then trough to trough adjusted by utilizing locations of the troughs in the signal (i.e., the signal starts and ends with a trough). Here, the trough to trough adjustment is performed for better subsequent window detection. In an embodiment, a set of data points can be lost during the trough to trough adjustment and can affect the locations associated with the set of peaks and the set of troughs. Further, at step 712, a signal detrending is performed by utilizing a cubic interpolation. Here, a baseline of the signal (basically the traces of the set of local minima) are detected and the detected baseline is utilized to eliminate the non-uniform drifts in the signal. Further, at step 714, peak-trough detection is performed on the detrended signal and the flow signal is obtained.

Further the signal analysis unit 250 of the pulmonary health monitoring system 200 can be configured to generate, the volumetric signal by processing the flow signal based on the numerical integration. Here, the flow signal is integrated with respect to time, by utilizing a trapezoidal rule based numerical integration to obtain the volumetric signal.

Further the signal analysis unit 250 of the pulmonary health monitoring system 200 can be configured to extract, the set of physiological features associated with the volumetric signal and the flow signal. Here, the set of physiological features includes an Inspiratory Time (IT), an Expiratory Time (ET), a Breathing Rate (BR), a Duty Cycle (DuCy), a Peak Inspiratory Flow (PIF), a Peak Expiratory Flow (PEF), a Time to Peak Inspiratory Flow (TPIF), a Time to Peak Expiratory Flow (TPEF), an Inspiratory Tidal Volume ($TV_{ins}$), an Expiratory Tidal Volume ($TV_{exp}$), an Inspiratory Velocity ($Vel_{ins}$), an Expiratory Velocity ($Vel_{exp}$). In an embodiment, the IT is a mean duration of all acquired inspiration phases in seconds. The ET is a mean duration of all acquired expiration phases in seconds. The BR is a number of breaths per minute, given by equation 11.

$$BPM = \frac{60}{IT + ET} \quad (11)$$

The DuCy is a mean of the ratios of inspiration time to total breathe time of all acquired breathe cycles and is given by equation 12, $$\text{Duty Cycle} = IT/(IT+ET) \quad (12)$$

The PIF is a maximum flow rate attained during the inspiratory period. The PEF is a maximum flow rate attained during the expiratory period. The TPIF is a mean time from onset to peak of inspiration of all inspiratory phases. The TPEF is a mean time from onset to peak of expiration of all expiratory phases. The $TV_{ins}$ is a mean volume of air inspired of all the acquired inspiration phases. The $TV_{exp}$ is a mean volume of air expired of all acquired expiration phases. The $Vel_{ins}$ is a mean velocity of inspiration from onset to peak of inspiration flow of all acquired inspiration phases. The $Vel_{exp}$ is a mean velocity of expiration from on set to peak of expiration flow of all the acquired expiration phases.

Further the signal analysis unit 250 of the pulmonary health monitoring system 200 can be configured to assess pulmonary health by analyzing the set of physiological features based on a machine learning technique. In an embodiment, a set of features are extracted from a plurality of sensors, including Peripheral capillary Oxygen Saturation (SpO2), Galvanic Skin Response (GSR) sensor, Electroencephalogram (EEG) sensor, and Photoplethysmography (PPG) sensor. Further, the set of features can be combined with the set of physiological features to obtain a set of combined features and the combined features can be analyzed for assessing the pulmonary health.

In an embodiment, the Locally Weighted Learning (LWL) based machine learning model is used for classification. The LWL classifier utilizes logistic regression internally. The LWL selects k-nearest neighbors for every observations and fit a hyperplane locally within the k-neighbors using the logistic regression. Since a set of neighbors of every observation can be with similar lungs capacity, a set of values associated with the set of physiological features need not be normalized. Moreover, in every k-neighbors of instances the set of values associated with the set of physiological features are expected to be highly correlated locally as the set of feature values belonging to a group with similar lung capacity. Hence, a logistic regression with ridge estimators, also called as a ridge regression is utilized. The ridge regression can be applied even in the presence of multi-collinearity among the set of physiological features.

In an embodiment, a binary variable S, indicating the subject to be either smoker or a nonsmoker can be modelled to identify a dependence of S on a vector x, where, x is a variable indicating the set of values associated with the set of physiological features for each trial of each subject is given by equation 13. Here, P is a number of physiological features utilized.

$$E(S)=P(S=1=g(\beta'S)) \quad (13)$$

where β' is a p vector of features. A common choice for g(t) is the inverse of the standard logistic distribution function, given by eqn. (14).

$$g(t)=\exp(t)/\{1+\exp(t)\} \quad (14)$$

In this case, equation 13 can be written as given in equation 15, $$\text{logit}(t)\{P(S=1|x)\}=\beta'x \quad (15)$$

where, logit(t)=log {t/(1−t)}. Equation 15 is a logistic regression model. Further, the ridge regression performs well in the presence of a multi-collinearity (two or more predictor variables i.e. feature are highly correlated). The multi-collinearity may lead to large standard error. Further, the ridge regression penalizes magnitude of regression coefficients based on L2 norm (Euclidian distance). Primary objective of ridge regression is to minimize Residual Sum of Squares (RSS)+alpha*sum of square of coefficients. Where alpha is the ridge parameter. Setting alpha=0 makes it simple linear regression. As alpha increases coefficients reduces in magnitude. The simple linear regression is as given in equation 15A.

$$Y_i = \Sigma_{j=1}^P X_{ij}\beta_j + \epsilon_i \quad (15A)$$

where, i is the normal errors with zero mean and variance. For N number of observations, let Y denote the N×1 matrix of all observation and X (a matrix of dimension N× p) whose columns corresponds to corresponding independent variable values. Further, the ridge estimator is given in equation 16, $$\hat{\beta}=\hat{\beta}_{ridge}=(X'X+\lambda_p)^{-1}X'Y \quad (16)$$

For Ordinary Least Square (OLS) solution, $\beta=(XX)^{-1}XY$, whereas for ridge regression, the ridge estimator is $\hat{\beta}_{ridge}=(X'X+\lambda_p)^{-1}X'Y$. This leads to a biased estimator but reduces variance. For ridge regression MSE=bias²+variance; hence even though bias is introduced, overall Mean Square Error (MSE) can decrease leading to better performance.

Figure 8:
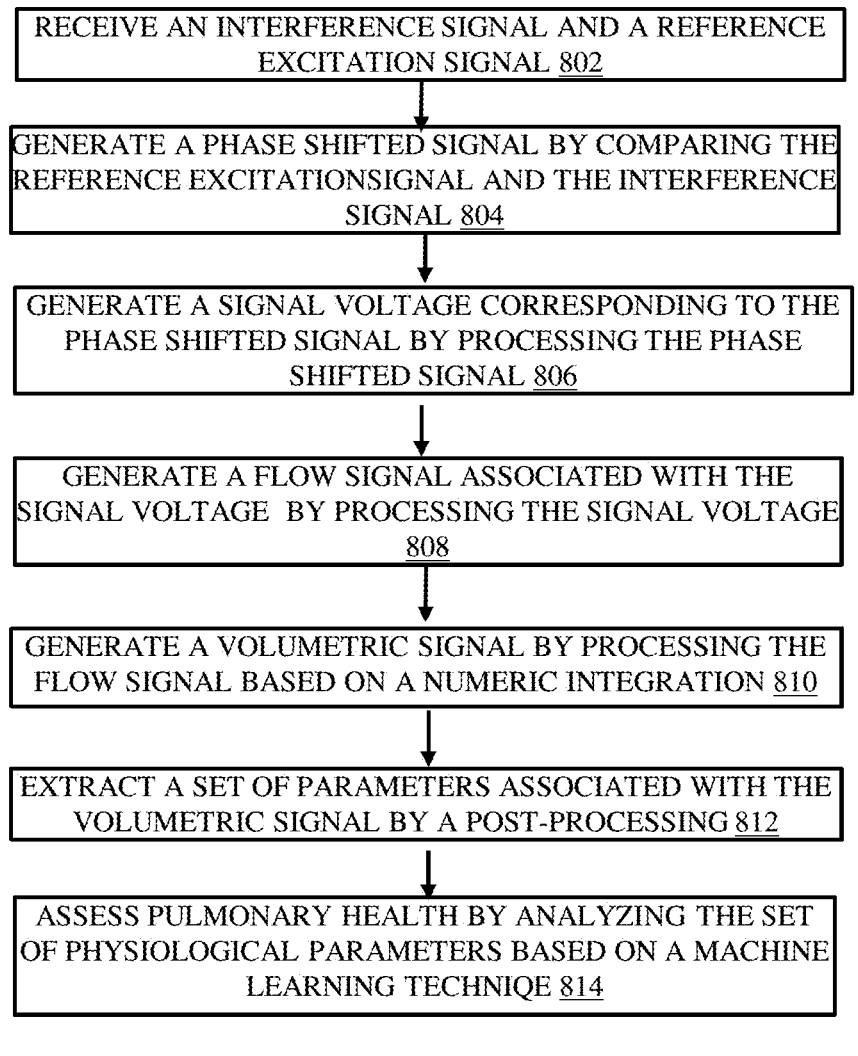
FIG. 8 illustrates an example flow diagram for pulmonary health monitoring, according to some embodiments of the present disclosure.

FIG. 8 illustrates a detailed flow diagram of a method 800 for the pulmonary health monitoring, according to some embodiments of the present disclosure. The method 800 may be described in the general context of computer executable instructions. Generally, computer executable instructions can include routines, programs, objects, components, data structures, procedures, modules, functions, etc., that perform particular functions or implement particular abstract data types. The method 800 may also be practiced in a distributed computing environment where functions are performed by remote processing devices that are linked through a communication network. The order in which the method 800 is described is not intended to be construed as a limitation, and any number of the described method blocks can be combined in any order to implement the method 800, or an alternative method. Furthermore, the method 800 can be implemented in any suitable hardware, software, firmware, or combination thereof.

At 802, the system 200 receives, by the one or more hardware processors, the interference signal, wherein the interference signal is the reference excitation signal, modified in accordance with the first signal. At 804, the system 200 generates, by the one or more hardware processors, the phase shifted signal by comparing the reference excitation signal and the interference signal. At 806, the system 200 generates, by the one or more hardware processors, the signal voltage corresponding to the phase shifted signal by processing the phase shifted signal. At 808, the system 200 generates, by the one or more hardware processors, the flow signal associated with the signal voltage by utilizing a set of peaks and a set of troughs associated with the signal voltage, wherein the set of peaks and the set of troughs are obtained by processing the signal voltage. Here, the mean value associated with the first signal is calculated and the Direct Current (DC) corrected signal voltage is obtained by subtracting the mean value from the signal voltage. Further, the filtered signal voltage is generated by eliminating anomalies from the DC corrected signal voltage and the set of peaks and the set of troughs are identified from the filtered signal voltage by utilizing a peak-trough detection technique. Further, the filtered signal voltage is aligned in a trough to trough basis based on the set of peaks and the set of troughs. Further, a the detrend signal is generated by eliminating the set of non-uniform drifts associated with the filtered signal voltage by tracking a baseline of the filtered signal voltage, wherein the baseline of the filtered signal voltage is identified by utilizing a cubic interpolation technique. Further, the peak trough associated with the detrend signal generated by identifying the local maxima and the local minima associated with the detrend signal and the flow signal is generated based on the peak trough. At 810, the system 200 generates, by the one or more hardware processors, the volumetric signal by processing the flow signal based on the trapezoidal rule based numerical integration technique. At 812, the system 200 extracts, by the one or more hardware processors, the set of physiological features associated with the volumetric signal. At 814, the system 200 assesses, by the one or more hardware processors, pulmonary health by analyzing the set of physiological features based on LWL ridge regression based machine learning technique. Here, the set of values associated with each physiological features is extracted from the set of physiological features for each observation associated with the subject. Further, the set of nearest neighbors associated with each observation is generated and the hyperplane is fitted on the set of nearest neighbors based on a regression. Further, the pulmonary health of the subject is classified based on the hyperplane.

In an embodiment, the system 200 is experimented as follows:

Data acquisition: In an embodiment, a complete tidal breathing analysis is done on data gathered from 20 healthy subjects of age ranging from 23-51 years, consisting of 6 female and 14 male. All the experimental procedure are Helsinki declaration complaint and are ethical clearance satisfied. The subjects are made to seat on a comfortable chair with back and arm rests. Initially, the objective and procedure of the experiment are explained to the subjects undergoing the experiment. Further, the subjects are instructed to tidally breathe in and blow out without any voluntary effort for 60 secs through the flow pipe 304 (refer FIG. 3). Three such trials, one trial each day for three consecutive days, are taken for each subject. During experimentation, the nose is closed using a nose clip, so that entire inhalation and exhalation occurs through mouth. The advantage of the present disclosure is that the technique does not require the subjects to respire forcefully and to hold breathes.

Computing tidal breathing features: In an embodiment, the set of physiological features in addition to the breathing rate and/or tidal volume can provide more insight towards pulmonary health monitoring. The set of physiological features values obtained from the flow signal and the volumetric signal are as shown in Table 1. In another embodiment, the set of features extracted from the plurality of sensors, including SpO2, GSR sensor, EEG sensor, and PPG sensor can be combined with the set of physiological features to obtain the set of combined features to obtain more accuracy in pulmonary health monitoring. In Table I, the average value for the set of physiological features, for three trials conducted for each of the subjects are given. Additionally, the standard deviation for the three trials are given in parenthesis. It can be seen that the standard deviation for all features are minimal, indicating that the intra-subject variance over the number of trials is very less.

TABLE I

| Sl. No | BR (BPM) | TI (s) | TE (s) | DuCy | PIF (L/s) | TPIF (s) | PEF (L/s) | TPEF (s) | $TV_{Ins}$ (L) | $TV_{exp}$ (L) | $Vel_{Ins}$ (m/s) | $Vel_{exp}$ (m/s) |
|---|---|---|---|---|---|---|---|---|---|---|---|---|
| 1 | 7.51 | 4.01 | 3.76 | 0.50 | 1.18 | 0.85 | 1.79 | 0.75 | 2.43 | 2.34 | 2.68 | 4.08 |
|   | (0.72) | (0.17) | (0.20) | (0.03) | (0 05) | (0.15) | (0.16) | (0.09) | (0.38) | (0.16) | (0.11) | (0.12) |
| 2 | 26.7 | 1.42 | 0.8 | 0.63 | 1.13 | 0.57 | 2.35 | 0.43 | 0.65 | 0.64 | 2.56 | 5.30 |
|   | (1.11) | (0.14) | (0.08) | (0.04) | (0.04) | (0.02) | (0.16) | (0.16) | (0.06) | (0.10) | (0.11) | (0.31) |
| 3 | 16.84 | 1.99 | 1.44 | 0.56 | 1.55 | 0.77 | 2.19 | 0.32 | 1.53 | 1.50 | 3.49 | 5.02 |
|   | (1.01) | (0.06) | (0.15) | (0.04) | (0.01) | (0.05) | (0.03) | (0.02) | (0.03) | (0.05) | (0.01) | (0.04) |
| 4 | 29.06 | 1.29 | 0.74 | 0.62 | 1.36 | 0.36 | 1.86 | 0.20 | 0.72 | 0.71 | 3.08 | 4.21 |
|   | (0.91) | (0.09) | (0.06) | (0.03) | (0.05) | (0.03) | (0.01) | (0.01) | (0.01) | (0.01) | (0.13) | (0.01) |
| 5 | 26.96 | 1.25 | 0.95 | 0.56 | 1.71 | 0.33 | 2.50 | 0.20 | 1.05 | 1.05 | 3.86 | 5.68 |
|   | (1.5) | (0.08) | (0.05) | (0.01) | (0.05) | (0.06) | (0.01) | (0.01) | (0.05) | (0.04) | (0.13) | (0.01) |
| 6 | 30.24 | 1.12 | 0.83 | 0.57 | 1.40 | 0.19 | 2.27 | 0.16 | 0.92 | 0.94 | 3.16 | 5.16 |
|   | (0.87) | (0.05) | (0.02) | (0.01) | (0.01) | (0.01) | (0.01) | (0.01) | (0.04) | (0.03) | (0.01) | (0.06) |
| 7 | 28.64 | 1.15 | 0.92 | 0.55 | 1.57 | 0.20 | 1.98 | 0.18 | 1.06 | 1.07 | 3.56 | 4.56 |
|   | (2.77) | (0.10) | (0.08) | (0.01) | (0.04) | (0.02) | (0.06) | (0.01) | (0.04) | (0.02) | (0.11) | (0.13) |
| 8 | 24.51 | 1.52 | 0.95 | 0.60 | 1.51 | 0.53 | 2.53 | 0.20 | 1.11 | 1.11 | 3.42 | 5.71 |
|   | (3.9) | (0.26) | (0.15) | (0.01) | (0.01) | (0.13) | (0.06) | (0.04) | (0.10) | (0.10) | (0.04) | (0.15) |
| 9 | 28.90 | 1.20 | 0.86 | 0.57 | 1.54 | 0.25 | 2.48 | 0.17 | 1.03 | 1.02 | 3.49 | 5.64 |
|   | (1.95) | (0.11) | (0.05) | (0.02) | (0.03) | (0.02) | (0.09) | (0.01) | (0.05) | (0.10) | (0.07) | (0.29) |
| 10 | 16.73 | 2.17 | 1.36 | 0.60 | 1.67 | 0.69 | 3.10 | 0.26 | 1.80 | 1.80 | 3.78 | 7.06 |
|   | (0.34) | (0.05) | (0.08) | (0.01) | (0.07) | (0.08) | (0.04) | (0.01) | (0.04) | (0.04) | (0.16) | (0.09) |
| 11 | 12.42 | 3.09 | 1.60 | 0.63 | 1.53 | 1.16 | 2.47 | 0.60 | 1.61 | 1.62 | 3.45 | 5.73 |
|   | (0.61) | (0.27) | (0.12) | (0.04) | (0.02) | (0.31) | (0.13) | (0.10) | (0.16) | (0.02) | (0.04) | (0.03) |
| 12 | 17.76 | 2.04 | 1.27 | 0.60 | 1.37 | 0.73 | 2.69 | 0.42 | 1.31 | 1.31 | 3.1 | 6.14 |
|   | (1.05) | (0.10) | (0.07) | (0.02) | (0.17) | (0.02) | (0.01) | (0.16) | (0.04) | (0.17) | (0.38) | (0.21) |
| 13 | 17.31 | 1.97 | 1.48 | 0.57 | 1.63 | 0.63 | 2.46 | 0.31 | 1.54 | 1.56 | 3.68 | 5.55 |
|   | (0.41) | (0.10) | (0.07) | (0.01) | (0.05) | (0.15) | (0.06) | (0.05) | (0.12) | (0.11) | (0.11) | (0.11) |
| 14 | 30.84 | 1.19 | 0.75 | 0.60 | 1.51 | 0.68 | 2.57 | 0.67 | 0.78 | 0.77 | 3.43 | 5.82 |
|   | (1.58) | (0.16) | (0.06) | (0.05) | (0.11) | (0.63) | (0.27) | (1.09) | (0.03) | (0.02) | (0.30) | (0.49) |
| 15 | 13.76 | 2.45 | 1.82 | 0.56 | 1.52 | 0.96 | 1.57 | 0.60 | 1.56 | 1.56 | 3.43 | 3.67 |

TABLE I-continued

| Sl. No | BR (BPM) | TI (s) | TE (s) | DuCy | PIF (L/s) | TPIF (s) | PEF (L/s) | TPEF (s) | $TV_{Ins}$ (L) | $TV_{exp}$ (L) | $Vel_{Ins}$ (m/s) | $Vel_{exp}$ (m/s) |
|---|---|---|---|---|---|---|---|---|---|---|---|---|
|    | (0.88) | (0.11) | (0.16) | (0.01) | (0.05) | (0.20) | (0.22) | (0.01) | (0.25) | (0.27) | (0.1) | (0.51) |
| 16 | 7.42 | 4.74 | 3.09 | 0.58 | 0.97 | 1.55 | 2.44 | 0.45 | 2.64 | 2.46 | 2.21 | 5.69 |
|    | (0.64) | (0.36) | (0.21) | (0.01) | (0.01) | (0.21) | (0.06) | (0.02) | (0.05) | (0.01) | (0.06) | (0.04) |
| 17 | 24.30 | 1.26 | 1.22 | 0.50 | 1.61 | 0.22 | 2.41 | 0.14 | 1.40 | 1.42 | 3.63 | 5.52 |
|    | (3.12) | (0.18) | (0.18) | (0.01) | (0.06) | (0.08) | (0.07) | (0.02) | (0.03) | (0.05) | (0.13) | (0.16) |
| 18 | 19.75 | 1.91 | 1.09 | 0.63 | 1.26 | 0.82 | 2.60 | 0.29 | 1.10 | 1.15 | 2.85 | 6.01 |
|    | (0.42) | (0.01) | (0.01) | (0.01) | (0.09) | (0.07) | (0.34) | (0.02) | (0.11) | (0.16) | (0.21) | (0.76) |
| 19 | 18.53 | 1.86 | 1.31 | 0.57 | 1.60 | 0.62 | 2.41 | 0.33 | 1.44 | 1.42 | 3.61 | 5.50 |
|    | (0.89) | (0.01) | (0.03) | (0.02) | (0.07) | (0.09) | (0.03) | (0.01) | (0.05) | (0.01) | (0.15) | (0.04) |
| 20 | 25.26 | 1.36 | 1.00 | 0.58 | 1.23 | 0.46 | 2.48 | 0.20 | 0.95 | 0.95 | 2.78 | 5.65 |
|    | (1.62) | (0.03) | (0.04) | (0.04) | (0.09) | (0.02) | (0.26) | (0.01) | (0.13) | (0.10) | (0.20) | (0.46) |

Feature level discriminability: In an embodiment, the set of physiological features, computed directly from the tidal breathing signal have been used to monitor compromised lungs of adults. The set of physiological features includes a set of primary physiological attributes pertaining to tidal breathing, along with their linear or proportional combination. In an embodiment, Fishers Linear Discriminant (FLD) method is utilized to inspect the effectiveness of the set of physiological attributes. Here, FLD is utilized to project the computed 12-dimensional feature-set to a single dimension. values obtained for mentioned metrics. Table I provides a comparison of the different classification models and lists the mean values of the set of well-known metrics and the percentage of accuracy of prediction metrics of classification along with their variation around the mean values for 10 trials in parenthesis. Here, L-O indicates Ordinary Logistic Regression, L-R indicates Logistic Regression with ridge regression, a plurality of values in bold fonts denote the highest value for each metric. Here, LWL ridge regression (LWL+L-R) provides best values for a majority of metrics.

TABLE II

| Scheme | % Acc | TPR | TNR | F | Kappa | AUC | AUP |
|---|---|---|---|---|---|---|---|
| LWL + L-R | 85.0 | 0.80 | 0.90 | 0.70 | 0.93 | 0.92 | 0.92 |
|  | (18.07) | (0.3) | (0.09) | (0.36) | (0.09) | (0.10) | (0.11) |
| LWL + L-O | 80.83 | 0.82 | 0.80 | 0.81 | 0.62 | 0.85 | 0.86 |
|  | (11.57) | (0.15) | (0.18) | (0.11) | (0.23) | (0.13) | (0.13) |
| L-R | 64.00 | 0.60 | 0.68 | 0.61 | 0.28 | 0.69 | 0.73 |
|  | (13.41) | (0.22) | (0.16) | (0.17) | (0.27) | (0.15) | (0.12) |
| L-O | 63.83 | 0.58 | 0.70 | 0.60 | 0.28 | 0.67 | 0.72 |
|  | (12.33) | (0.22) | (0.16) | (0.18) | (0.25) | (0.14) | (0.13) |

Figure 9:
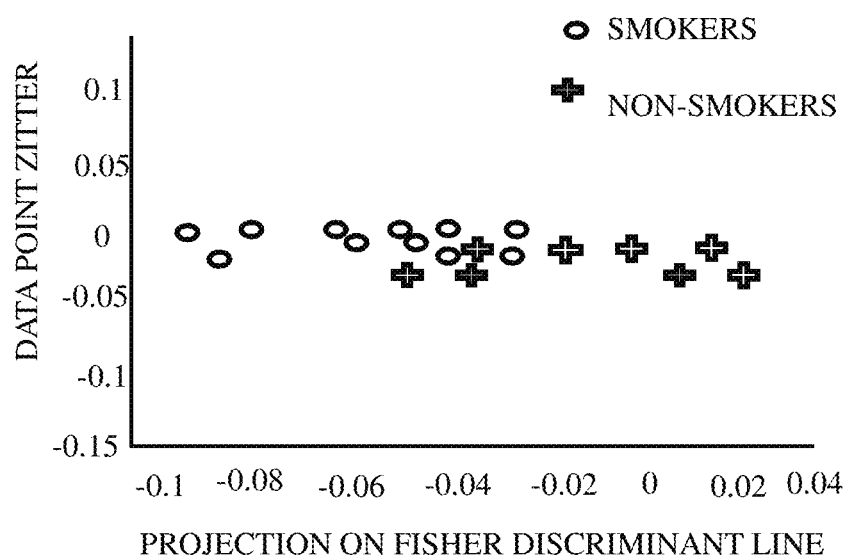
FIG. 9 illustrates an example plot showing a set of projected features on the Fisher's Linear Discriminant Line, according to some embodiments of the present disclosure.

FIG. 9 illustrates an example plot showing the set of projected features on the Fisher's Linear Discriminant Line, according to some embodiments of the present disclosure. Here, the y-axis values are given a random and deliberate spread for visual aid and the x-axis presents the value of the projection. The plot shows formation of two clusters (represented as plus and thick dots) with some overlaps. Here, there is a overlap and the overlap indicates usefulness of the tidal breathing based features. Although, FLD could be used for classification, it may lead to a weak classifier. In order to obtain higher accuracy and precision we have employed a superior classifier as discussed in the following sub sections.

Selection of ridge Regression for LWL: In an embodiment, LWL-ridge classifier is compared with other three closely related variants of LWL classifier for validation of classification methods. The performance of all variants of LWL classification schemes on the acquired dataset using 5 fold cross validation scheme and 10 runs for each selected folds is evaluated. In an embodiment, an open source WEKA machine learning platform is utilized to run all the LWL classifiers with the associated default parameter values. Apart from percentage of accuracy (% Acc) of prediction, a set of well-known metrics of classifiers are investigated. The set of well-known metrics includes a True Positive Rate (TPR), a True Negative Rate (TNR), F value, Kappa statistics, Area Under Receiver Operating Characteristic Curve (AUC) and Area Under Precision-Recall Curve (AUP). A best classifier is chosen among these based on Determination of LWL-Ridge Parameters: k and $\hat{\beta}$: In an embodiment, two parameters of LWL+L-R (LWL-ridge) are tuned in an attempt to attain most effective classification performance. The two parameters are tuned for particular choice of classes (smoker and non-smoker) and the k value in the k-nearest neighbors of LWL and the ridge parameter ($\hat{\beta}$) value of ridge regression are collected. Here, a random-split on the data with varying split, k and values are compared and the obtained results are reported in Table III.

TABLE III

| Choices of | T = 1/t of the total instances (i.e., 60 × 1/t) and t ∈ {2, 3, . . . 7} | | | | |
|---|---|---|---|---|---|
| {k, $\hat{\beta}$} | 1/3 | 1/4 | 1/5 | 1/6 | 1/7 |
| {10, $10^{-5}$} | 65 | 73.33 | 100 | 50 | 88.89 |
| {10, $10^{-4}$} | 85 | 80 | 100 | 70 | 88.89 |
| {10, $10^{-3}$} | 85 | 80 | 100 | 70 | 88.89 |

Figure 10:
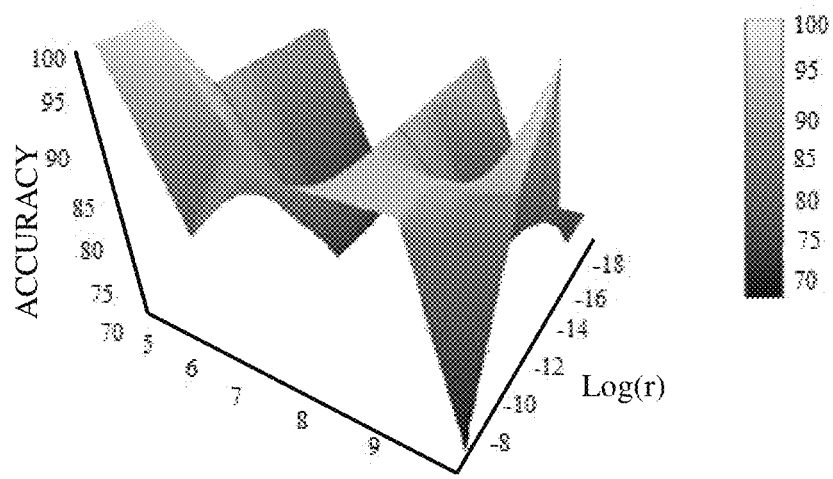
FIG. 10 illustrates an example surface plot for a set of splits and accuracy, according to some embodiments of the present disclosure.

In an embodiment, the three observations as shown in Table III indicates that the LWL ridge classifier performs best when 1/5 of the total dataset are taken as test cases (80% training and 20%-test case). To choose the best set of k, out of these three choices, as investigated, the accuracy (in percentage) is around the 80-20 (1/5 of entire data for test) split. FIG. 10 illustrates an example surface plot for a set of splits and accuracy, according to some embodiments of the present disclosure.

In an embodiment, calibration of the theoretical value for F (G, $K_0$) can be explained as follows: A system level calibration can be utilized to determine exact value of the term F (G). In the absence of a medically rated and/or commercially available tidal flow measuring device, the blow device is calibrated against a standard hot wire anemometer.

Figure 11:
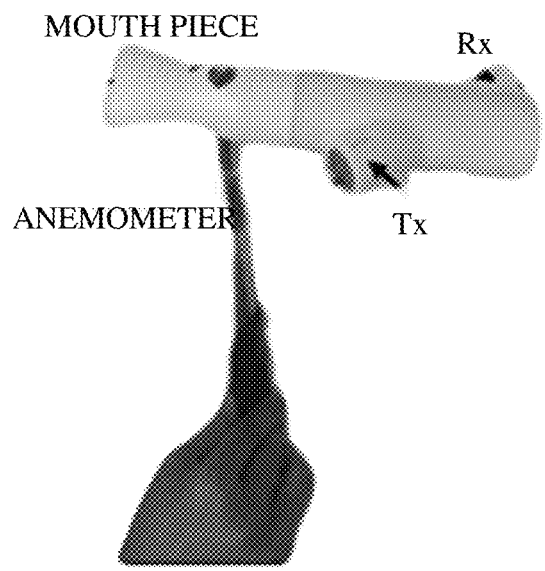
FIG. 11 illustrates a calibration arrangement of the blow device together with an anemometer, according to some embodiments of the present disclosure.
Figure 12:
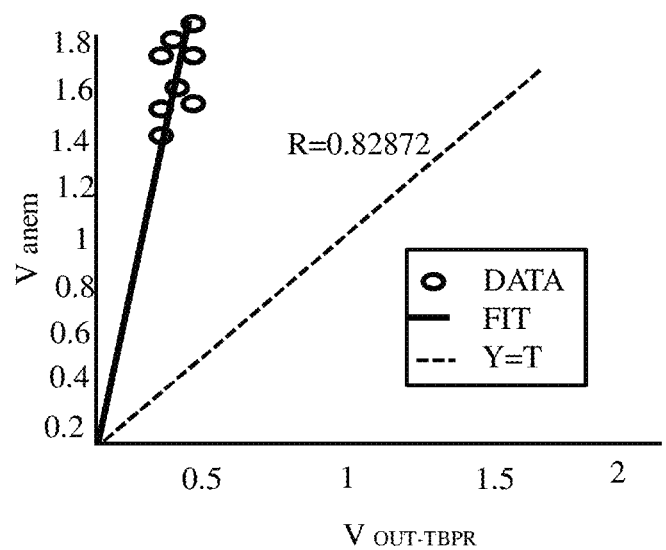
FIG. 12 illustrates an example plot between the signal voltage (VOUR_TBPR) and an anemometer flow velocity (vanem), according to some embodiments of the present disclosure.

In an embodiment, the blow device is a direct measure of respiration flow and requires the subjects to put the flow pipe in their mouth and breathe through it. FIG. 11 illustrates a calibration arrangement of the blow device together with an anemometer, according to some embodiments of the present disclosure. Now referring to FIG. 11, the calibration arrangement includes the anemometer and the blow device. The sensor probe of the anemometer is attached in the detachable mouth-piece of the blow device at an angle zero degree to the blow pipe. Further, the signal voltage output of the blow device is recorded and sampled at 100 Hz. Here, an airflow velocity measured by the anemometer is sampled at 1 Hz. Here, when a subject breathes through the calibration blow pipe arrangement shown in FIG. 11, the velocity recorded by the anemometer is the measure of inhalation/exhalation velocity which is the input to the breathe signal unit of the blow device. The breathe signal unit of the blow device generates the output signal voltage corresponding to the respective flow velocity (vanem) recorded by the anemometer. Further, the signal voltage is low pass filtered at 0.5 Hz and down-sampled at 1 Hz by taking the median value of every 100 samples of the filtered signal voltage. For example, 100 samples are taken around every time-instances recorded by the anemometer to avoid any microsecond level misalignment between the two sensor data. Subjects are instructed to tidally breathe through the calibration blow pipe arrangement. A first order polynomial regression curve is fitted between the Signal voltage (VOUR_TBPR) and vanem to determine the corrected (G), $F_{corr}$ (G) by computing the slope of the regression line. Further FIG. 12 illustrates an example plot between VOUR_TBPR and the anemometer flow velocity (vanem), according to some embodiments of the present disclosure. Now referring to FIG. 12, the slope of the regression line $F_{corr}$ (G) is, for example, 4.34 (the theoretically value is 4.83). Further, the flow rate (Q) is computed with $F_{corr}$ (G)=4.34 and the flow rate (Q) is given by equation 17, $$Q = F_{corr}(G) V_{OUT} \pi r_1^2 \cdot 10^3 \text{ (in L/sec)} \tag{17}$$

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Various embodiments disclosed methods and system for pulmonary health monitoring are able to provide an end-to-end solution for assessing the pulmonary health of the subject. The blow device with ultrasonic phase detection technique available in the present disclosure is capable of capturing very sensitive tidal signal and thus provides a cost effective solution for the pulmonary health monitoring. Further, LWL-ridge regression based machine learning technique with multiple physiological features increased the accuracy of the system 200.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for pulmonary health monitoring, the method comprising:
   receiving, by one or more hardware processors, an interference signal, wherein the interference signal is a reference excitation signal modified in accordance with a first signal;
   generating, by the one or more hardware processors, a phase shifted signal by comparing the reference excitation signal and the interference signal;
   generating, by the one or more hardware processors, a signal voltage corresponding to the phase shifted signal by processing the phase shifted signal;
   generating, by the one or more hardware processors, a flow signal associated with the signal voltage by utilizing a set of peaks and a set of troughs associated with the signal voltage, wherein the set of peaks and the set of troughs are obtained by processing the signal voltage, by:
      calculating a mean value associated with the first signal;
      generating a Direct Current (DC) corrected signal voltage by subtracting the mean value from the signal voltage;
      generating a filtered signal voltage by eliminating anomalies from the DC corrected signal voltage;
      identifying a set of peaks and a set of troughs from the filtered signal voltage by utilizing a peak-trough detection technique;
      aligning the filtered signal voltage in a trough to trough basis based on the set of peaks and the set of troughs;
      generating a detrend signal by eliminating a set of non-uniform drifts associated with the filtered signal voltage by tracking a baseline of the filtered signal voltage, wherein the baseline of the filtered signal voltage is identified by utilizing a cubic interpolation technique;
      detecting a peak trough associated with the detrend signal by identifying a local maxima and a local minima associated with the detrend signal; and
      generating the flow signal based on the peak trough;
   generating, by the one or more hardware processors, a volumetric signal by processing the flow signal based on a trapezoidal rule based numerical integration technique;
   extracting, by the one or more hardware processors, a set of physiological features associated with the volumetric signal and the flow signal; and
   assessing, by the one or more hardware processors, pulmonary health by analyzing the set of physiological features based on a ridge regression based machine learning technique.

2. The processor implemented method of claim 1, wherein the step of assessing pulmonary health by analyzing the set of physiological features based on a machine learning technique further comprises:
   receiving a set of values associated with each physiological features from the set of physiological features for each observation associated with a subject;
   identifying a set of nearest neighbors associated with each observation;
   fitting a hyperplane on the set of nearest neighbors based on a regression; and
   classifying the pulmonary health of the subject based on the hyperplane.

3. A pulmonary health monitoring system, the system comprising:
   one or more memories comprising programmed instructions and a repository for storing a first signal, a reference excitation signal, an interference signal, a phase shifted signal and a set of features associated with a volumetric signal;
   one or more hardware processors operatively coupled to the one or more memories, wherein the one or more hardware processors are capable of executing the programmed instructions stored in the one or more memories;
   a blow device to generate a phase shifted signal corresponding to the first signal, wherein the blow device comprises a flow pipe and a breathe signal unit; and
   wherein the one or more hardware processors are configured to:
      generate, a signal voltage corresponding to the phase shifted signal by processing the phase shifted signal;
      generate, a flow signal associated with the signal voltage by utilizing a set of peaks and a set of troughs associated with the signal voltage, wherein the set of peaks and the set of troughs are obtained by processing the signal voltage by:
         calculating a mean value associated with the first signal;
         generating a Direct Current (DC) corrected signal voltage by subtracting the mean value from the signal voltage;
         generating a filtered signal voltage by eliminating anomalies from the DC corrected signal voltage;
         identifying a set of peaks and a set of troughs from the filtered signal voltage by utilizing a peak-trough detection technique;
         aligning the filtered signal voltage in a trough to trough basis based on the set of peaks and the set of troughs;
         generating a detrend signal by eliminating the set of non-uniform drifts associated with the filtered signal voltage by tracking a baseline of the filtered signal voltage, wherein the baseline of the filtered signal voltage is identified by utilizing a cubic interpolation technique;
         detecting a peak trough associated with the detrend signal by identifying a local maxima and a local minima associated with the detrend signal; and
         generating the flow signal based on the peak trough;
      generate, a volumetric signal by processing the flow signal based on a trapezoidal rule based numerical integration technique;
      extract, a set of physiological features associated with the volumetric signal and the flow signal; and
      assess, pulmonary health by analyzing the set of physiological features based on a ridge regression based machine learning technique.

4. The system of claim 3, wherein the flow pipe of the blow device further comprises:

a blow pipe, wherein the blow pipe further comprises a first hollow pipe cross coupled to a second hollow pipe inclined at a predefined angle with the first hollow pipe;

a mouth piece detachably attached to a first end of the first hollow pipe to receive the first signal; and a transmitter transducer hosted at a first end of the second hollow pipe to generate the reference excitation signal and a receiver transducer hosted at a second end of the second hollow pipe to receive the interference signal, wherein the interference signal is the reference excitation signal, modified in accordance with the first signal.

5. The system of claim 3, wherein the one or more hardware processors are configured to generate the phase shifted signal corresponding to the first signal by comparing the reference excitation signal and the interference signal.

6. The system of claim 3, wherein the one or more hardware processors are configured to assess the pulmonary health based on the machine learning technique based analysis of the set of physiological features by:

receiving a set of values associated with each physiological features from the set of physiological features for each observation associated with a subject;

identifying a set of nearest neighbors associated with each observation;

fitting a hyperplane on the set of nearest neighbors based on a regression; and classifying the pulmonary health of the subject based on the hyperplane.

7. One or more non-transitory machine readable information storage mediums comprising one or more instructions which when executed by one or more hardware processors causes:

receiving, by one or more hardware processors, an interference signal, wherein the interference signal is a reference excitation signal modified in accordance with a first signal;

generating, by the one or more hardware processors, a phase shifted signal by comparing the reference excitation signal and the interference signal;

generating, by the one or more hardware processors, a signal voltage corresponding to the phase shifted signal by processing the phase shifted signal;

generating, by the one or more hardware processors, a flow signal associated with the signal voltage by utilizing a set of peaks and a set of troughs associated with the signal voltage, wherein the set of peaks and the set of troughs are obtained by processing the signal voltage by:

calculating a mean value associated with the first signal;

generating a Direct Current (DC) corrected signal voltage by subtracting the mean value from the signal voltage;

generating a filtered signal voltage by eliminating anomalies from the DC corrected signal voltage;

identifying a set of peaks and a set of troughs from the filtered signal voltage by utilizing a peak-trough detection technique;

aligning the filtered signal voltage in a trough to trough basis based on the set of peaks and the set of troughs;

generating a detrend signal by eliminating the set of non-uniform drifts associated with the filtered signal voltage by tracking a baseline of the filtered signal voltage, wherein the baseline of the filtered signal voltage is identified by utilizing a cubic interpolation technique;

detecting a peak trough associated with the detrend signal by identifying a local maxima and a local minima associated with the detrend signal; and generating the flow signal based on the peak trough;

generating, by the one or more hardware processors, a volumetric signal by processing the flow signal based on a trapezoidal rule based numerical integration technique;

extracting, by the one or more hardware processors, a set of physiological features associated with the volumetric signal and the flow signal; and assessing, by the one or more hardware processors, pulmonary health by analyzing the set of physiological features based on a ridge regression based machine learning technique.

* * * * *